(12) United States Patent
Bowers

(10) Patent No.: US 6,289,745 B1
(45) Date of Patent: Sep. 18, 2001

(54) HIGH TEMPERATURE INSERTION TYPE FLOW ELEMENT AND MOUNTING EXTENSION

(76) Inventor: James Bowers, 19615 Lake Rd., Rocky River, OH (US) 44116

( * ) Notice: Subject to any disclaimer, the term of this patent is extended or adjusted under 35 U.S.C. 154(b) by 0 days.

(21) Appl. No.: 09/305,266

(22) Filed: May 4, 1999

(51) Int. Cl.[7] ............................................... G01F 1/46
(52) U.S. Cl. ............................................... 73/861.66
(58) Field of Search ........................... 73/861.66, 861.52, 73/861.53, 861.65

(56) References Cited

U.S. PATENT DOCUMENTS

| | | |
|---|---|---|
| 1,250,238 | 12/1917 | Spitzglass . |
| 3,685,355 | 8/1972 | Debaun . |
| 4,297,900 | 11/1981 | Brandt, Jr. . |
| 4,344,330 | 8/1982 | Renken . |
| 4,372,171 * | 2/1983 | Bradt, Jr. ........................... 73/861.66 |
| 4,498,347 * | 2/1985 | Grantham et al. ................ 73/861.66 |
| 4,602,514 | 7/1986 | Kurrle . |
| 4,750,370 | 6/1988 | Ossyra . |
| 5,481,925 | 1/1996 | Woodbury . |
| 5,483,839 | 1/1996 | Meunier . |
| 5,665,923 * | 9/1997 | Kelley ............................... 73/861.66 |
| 5,736,651 * | 4/1998 | Bowers ............................. 73/861.66 |
| 6,044,716 * | 4/2000 | Yamamoto ....................... 73/861.66 |

* cited by examiner

Primary Examiner—Benjamin R. Fuller
Assistant Examiner—Jewel V. Thompson
(74) Attorney, Agent, or Firm—John D. Gugliotta

(57) ABSTRACT

Disclosed is a high temperature insertion type flow element and mounting extension assembly for a gas flow measuring device. Designed to overcome the drawbacks associated with compensating for differential thermal expansion between the element and the duct wall, the element consists of an otherwise conventional insertion type flow element, that incorporates the use of a mounting extension assembly and an expansion fitting. The mounting extension positions the element head in an offset manner from the gas duct, placing the element head in a position away from any insulating materials encasing the duct, allowing for convenient access to the instrumentation and cleaning ports. The expansion fitting stabilizes the element tubes within the duct while absorbing any differential thermal expansion.

18 Claims, 8 Drawing Sheets

HIGH TEMPERATURE INSERTION TYPE FLOW ELEMENT AND MOUNTING EXTENSION

BACKGROUND OF THE INVENTION

1. Field of the Invention

The present invention relates generally to insertion type gas flow meters and, more particularly, to a high temperature insertion type flow element with a mounting extension.

2. Description of the Related Art

The instrumentation and process control industry has recognized the use of the Pitot tube as a reliable device for measuring the volumetric flow of both liquids and gasses for many years. The Pitot tube operates based upon the principal that when a fixed probe is inserted into piping or duct work containing a moving fluid, the total pressure sensed by the probe is the sum of the static pressure exerted by the fluid, whether in motion or at rest, and the dynamic pressure equivalent to the kinetic energy of the fluid in motion. Conventional Pitot tube arrangements provide measurement of both the static and total pressure of the flowing fluid, the difference between which is the dynamic pressure. This differential pressure, i.e. the dynamic pressure, is directly related to and can be used to calculate the linear flow rate within the piping or duct work. The volumetric flow rate of the fluid is determined by multiplying the linear flow rate by the cross-sectional area of the conduit.

The Pitot tube is particularly useful in measuring gas flows in pipes or ducts with a large cross-sectional area because a Pitot tube causes negligible pressure loss within the conduit. In application, it is well known that flow rates, and thus dynamic pressures, within a conduit are not uniform. Affected by variables such as the Reynolds number of the particular gas and turbulence caused by wall surface roughness, dampers, elbows and other fittings, the flow rate/dynamic pressure is generally higher toward the center of the conduit and lower towards the outer extremes. This phenomenon is described in terms of a velocity profile, wherein a vector representation of the linear velocities at various points within the conduit defines a characteristic profile curve. The dynamic nature of the velocity profile precludes accurate measurement with a single Pitot tube. Rather, an accurate measurement of the flow within the conduit is obtained by placing Pitot tubes at various positions on a cross-sectional plane, sampling the dynamic pressure at various points across the velocity profile, averaging them, and using the result to calculate a volumetric flow rate.

A popular type of Pitot tube arrangement is that of the insertion type flow elements. Typical insertion type flow elements consist of a dynamic pressure sensing Pitot tube and a static pressure sensing Pitot tube connected to an element head having connections that allow for connecting the individual tubes to instrumentation devices. Depending upon the size of the duct, any number of elements can be inserted, traversing the interior cross-section of the duct at varying locations so as to account for the flow profile within the duct. The individual dynamic and static pressures are then joined at a common header or manifold so that an overall differential pressure can be determined. Use of the insertion type flow element is advantageous in that the element is suited for insertion through a duct wall and thus requires minimal installation efforts. Depending upon variables such as the size of the duct, temperature and velocity of the gasses passing therethrough, the insertion type flow element is fit with outboard support wherein it is anchored to the duct wall both at the element head end and at the opposite end of the Pitot tubes. In high temperature applications, however, a vast majority of insertion type flow element installations are of the type having an outboard support. While the insertion type flow element provides accurate measurements and ease of installation, its use does give way to some persistent problems that have, until now, gone unsolved.

One particular problem can occur in airflow applications in which particulate concentrations are heavy. In such applications Pitot tubes can become clogged, creating inaccuracies in flow measurement wherein the element senses an erroneous gas flow. In these applications, there is a need to frequently clean clogged tubes in order to maintain an accurate gas flow measurement. Typically, the element must be taken out of service for cleaning, which is labor intensive, time consuming and, thus, extremely undesirable. An adequate solution for this problem has yet to be addressed in the industry.

Another particular problem occurs in applications where the flow rate of hot gasses are measured, wherein thermal expansion causes a differential expansion between the Pitot tubes and the duct wall. When this occurs, the expansion of the Pitot tubes in the longitudinal direction is greater than that of the cross-sectional expansion of the duct wall. Being that the element is typically fit with outboard support, as a result, the Pitot tubes either fail themselves or the welded bead holding them in place fails. The present invention is directed toward a high temperature mounting extension for use in conjunction with an insertion type Pitot tube flow element having an outboard support that incorporates high temperature packing that allows for thermal differential expansion that remedies the above mentioned problems associated with conventional installation practices.

A search of the prior art produced the following inventions related to Pitot tube gas flow measuring devices:

U.S. Pat. No. 1,250,238, issued in the name of Spitzglass;

U.S. Pat. No. 3,685,355, issued in the name of DeBaun;

U.S. Pat. No. 4,297,900, issued in the name of Brandt, Jr.;

U.S. Pat. No. 4,344,330, issued in the name of Renken et al.;

U.S. Pat. No. 4,602,514, issued in the name of Kurrle et al.;

U.S. Pat. No. 4,750,370, issued in the name of Ossyra;

U.S. Pat. No. 5,481,925, issued in the name of Woodbury; and

U.S. Pat. No. 5,483,839, issued in the name of Meunier.

While all of these patents describe devices incorporating the use of a Pitot tube device to determine the volumetric flow rate of gasses in a conduit or the like, none of them address the specific problems associated with tube cleaning or differential thermal expansion in an insertion type flow element.

Also, of considerable relevance is U.S. Pat. No. 5,736,651, issued in the name of Bowers, the present inventor. In this patent, disclosed is a high temperature gas flow sensing element wherein a frame structure supports a Pitot tube array that spans its interior cross-section. The internal dimensions of the frame are the same as that of the conduit in which the gas flow is to be measured. Inserted in line with the conduit, the gasses in the conduit flow through the element, thus producing a flow measurement. The Bowers flow sensing element incorporates the use of exterior access ports to allow for cleaning of the Pitot tubes without removing the element.

Additionally, pliable, high temperature packing material is used to secure the Pitot tubes within the element while permitting them to expand and contract. While many solutions to the problems associated with high temperature flow measurement are incorporated into this invention, the disclosure does not address the specific problems encountered when dealing with an insertion type element. As such, the present invention is sufficiently novel and non-obvious so as to distinguish it from the prior art, including the present inventor's own prior art.

SUMMARY OF THE INVENTION

Briefly described according to the preferred embodiment of the present invention, disclosed is a high temperature insertion type flow element and mounting extension assembly for a gas flow measuring device. Designed to overcome the drawbacks associated with compensating for differential thermal expansion between the element and the duct wall, the element consists of an otherwise conventional insertion type flow element, having dynamic and static pressure sensing Pitot tubes, that incorporates the use of a mounting extension assembly at the element head end and an expansion fitting at the end opposite the element head. The flow element is secured to an existing gas duct by boring a hole in the duct sidewall and inserting the element such that the Pitot tubes span the interior cross-section thereof. Using conventional fastening means such as bolt-type fasteners or welding, the mounting extension and the expansion fitting are secured to opposite exterior surfaces of the duct. The mounting extension positions the element head in an offset manner from the gas duct, placing the element head in a position away from any insulating materials encasing the duct, allowing for convenient access to the instrumentation and cleaning ports. The expansion fitting stabilizes the Pitot tubes within the duct while absorbing any differential thermal expansion. The flow element is designed and installed so as to cause a minimal amount of disturbance to the flow within the duct.

Therefore, it is an object of the invention to provide a high temperature insertion type flow element and mounting extension that provides accurate flow measurement of high temperature gasses within a duct.

It is another object of the invention to provide a high temperature insertion type flow element and mounting extension that allows for differential thermal expansion between the Pitot tubes and the duct wall.

It is another object of the invention to provide a high temperature insertion type flow element and mounting extension that positions the element head away from the insulation packing often found on the exterior surface of high temperature duct work, providing convenient access to the instrumentation and cleaning ports thereof.

It is another object of the invention to provide a high temperature insertion type flow element and mounting extension wherein a minimal amount of disturbance is caused to the gas flow within the duct work.

Finally, it is an object of the invention to provide a high temperature insertion type flow element and mounting extension used in ducts of varying size and cross-sectional shape.

LIST OF REFERENCE NUMBERS

- 20 High Temperature Flow Element
- 21 Element Head
- 22 Mounting Extension
- 23 Element Tubes
- 24 Outboard Support
- 25 Instrumentation Ports
- 26 Cleaning Ports
- 30 Outboard Support Fitting
- 31 Outboard Access Port
- 32 Outboard Support Plate
- 35 Tubular Housing
- 36 Element Head Support Flange
- 37 Mounting Extension Support Flange
- 38 Element Tube Aperture
- 39 Second Element Tube Aperture
- 40 Fastener Apertures
- 44 Element Head Mounting Plate
- 45 Welded Bead
- 46 Element Tube Apertures
- 50 Element Head Gasket
- 51 Extension Housing Sealing Plate
- 52 Extension Housing Sealing Gasket
- 60 Compression Fitting
- 61 Cap
- 65 Element Tube Support Bracket
- 66 Cross-Member
- 67 Anchoring Rod
- 70 High-Temperature Packing
- 71 Compression Sleeve
- 72 Compression Cap
- 80 Duct
- 81 Duct Walls
- 82 Insertion Apertures
- 85 Insulating Materials

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
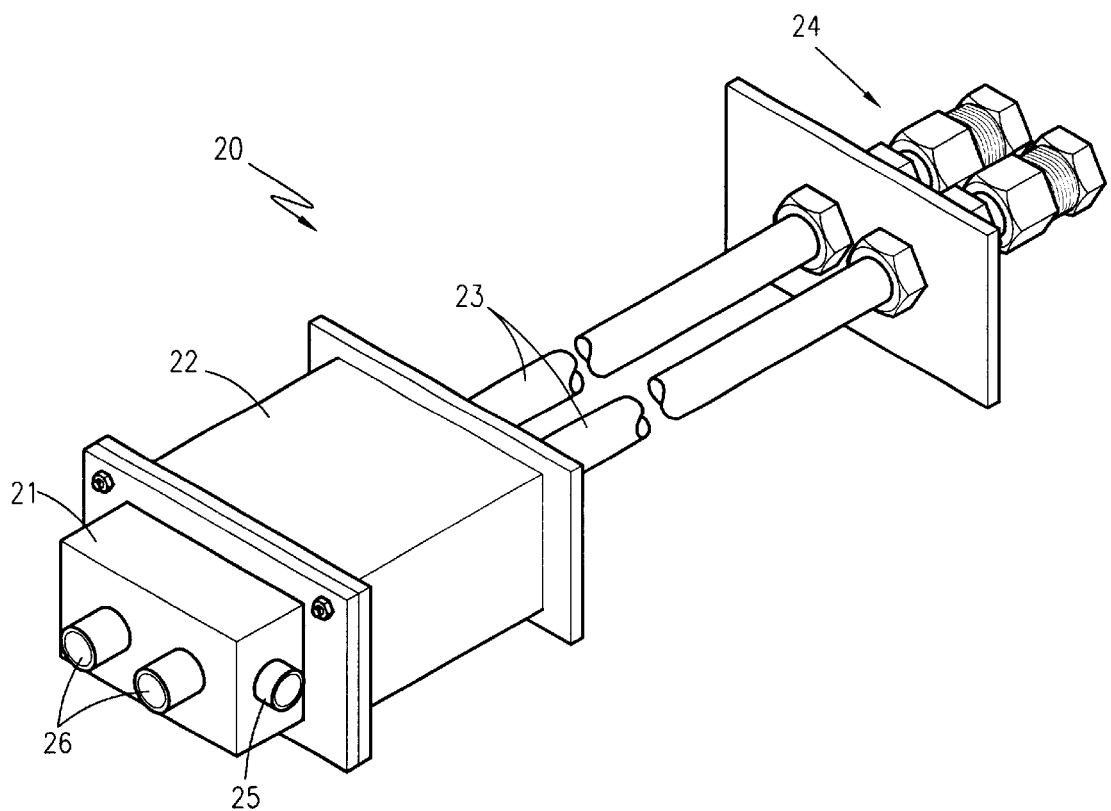
FIG. 1 is a perspective view of the high temperature insertion type flow element and mounting extension, according to the preferred embodiment of the present invention.

Referring now to FIG. 1, depicted is the high temperature insertion type flow element and mounting extension, hereinafter high temperature flow element 20, according to the preferred embodiment of the present invention. The high temperature flow element 20 consists, in general of four parts: an element head 21, a mounting extension 22, element tubes 23 and an outboard support 24. The element head 21 serves a manifold-type function, having instrumentation ports 25 to which instrumentation devices (not shown) are attached and cleaning ports 26 through which the element tubes can be accessed for cleaning and maintenance purposes. The mounting extension 22 allows the element head 21 to be mounted to a duct (not shown in FIG. 1) in an offset rather than abutting manner, so as to provide easy access to the element head 21 and not causing interference with the duct's insulating materials. The element tubes 23 span the interior cross-section of the duct and provide a differential measurement of the static and dynamic pressures within the duct. The outboard support 24 stabilizes the element tubes 23 within the duct, preventing vibration, and incorporating a design that serves to absorb differential expansion between the duct walls and the element tubes 23.

Figure 2A:
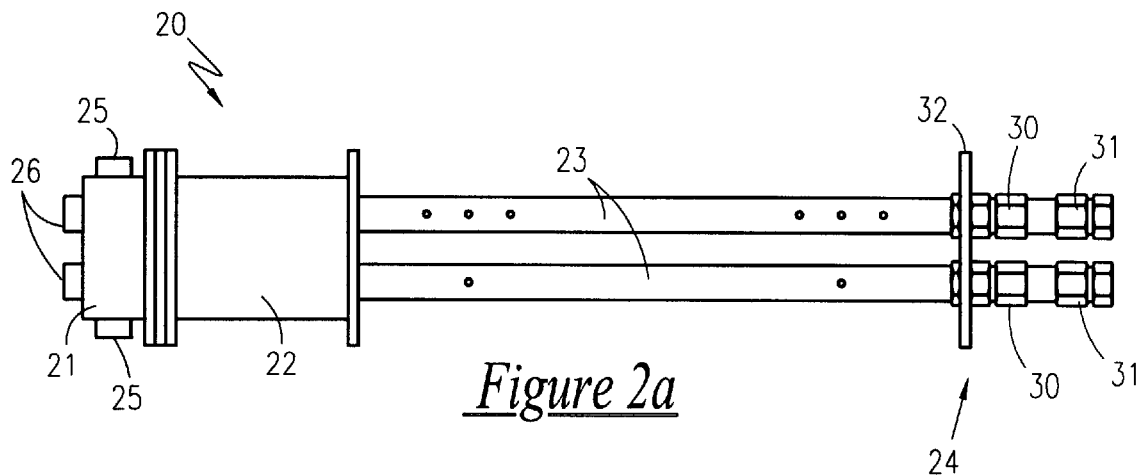
FIG. 2a is a horizontal plan view of the high temperature insertion type flow element and mounting extension with outboard access ports and supports, according to the preferred embodiment of the present invention.
Figure 2B:
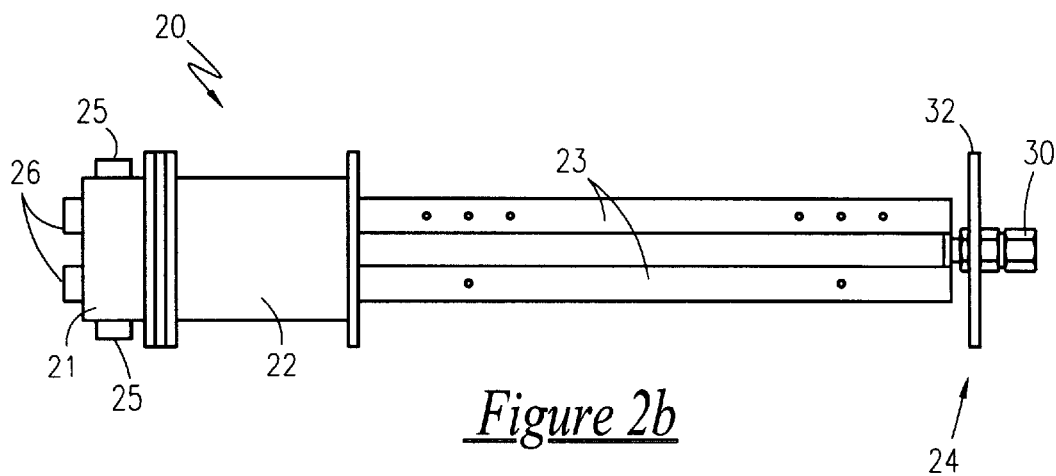
FIG. 2b is a horizontal plan view of the high temperature insertion type flow element and mounting extension with outboard end supports, according to the preferred embodiment of the present invention.

Referring now to FIGS. 2a and 2b, depicted is the high temperature flow element 20 having slight variations in the design and function of the outboard support 24. In FIG. 2a, the outboard support 24 consists of an outboard support fitting 30 and an outboard access port 31 for each element tube 23. The outboard support fitting secures the element tubes 23 to an outboard support plate 32 that is secured to the exterior surface of the duct wall (not shown in FIG. 2a or 2b) via conventional fastening means. The outboard access port 31 allows for cleaning and maintenance of the element tubes 23 from the end opposite the mounting extension 22 and element head 21. In FIG. 2b, the outboard support 24 consists of a single outboard support fitting 30, that stabilizes both of the element tubes 23, securing them to the outboard support plate 32. In both configurations, the outboard support fitting 30 consists of an expansion fitting designed to absorb the differential expansion between the element tubes 23 and the duct sidewall. Therefore, the differences in the configuration of the high temperature flow element 20 depicted in FIGS. 2a and 2b are not material to the operation of the present invention in terms of providing support for the element tubes 23 and absorbing differential expansion. The design and operation of the outboard support 24 and the outboard support fittings 30 will be discussed in further detail herein below.

Figure 3A:
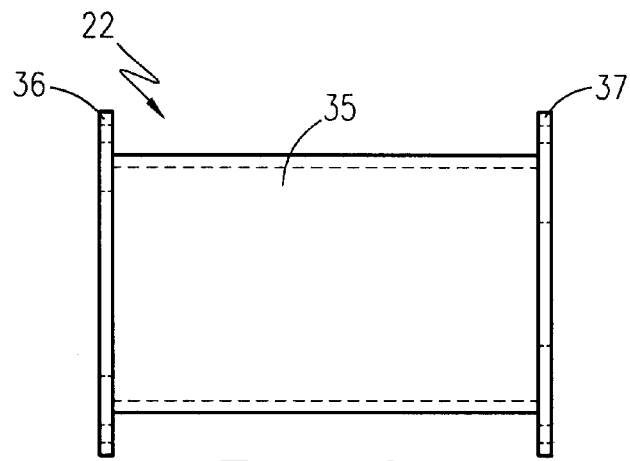
FIG. 3a is side view of the mounting extension portion of the high temperature insertion type flow element and mounting extension with outboard end supports, according to the preferred embodiment of the present invention.
Figure 3B:
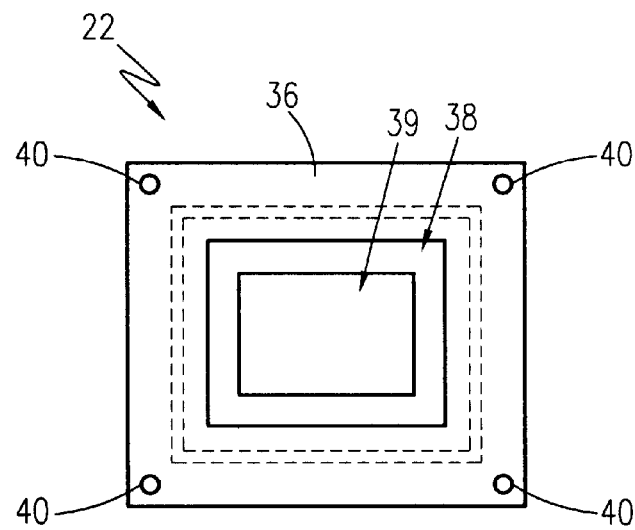
FIG. 3b is left end view of the mounting extension portion of the high temperature insertion type flow element and mounting extension with outboard end supports, according to the preferred embodiment of the present invention.
Figure 3C:
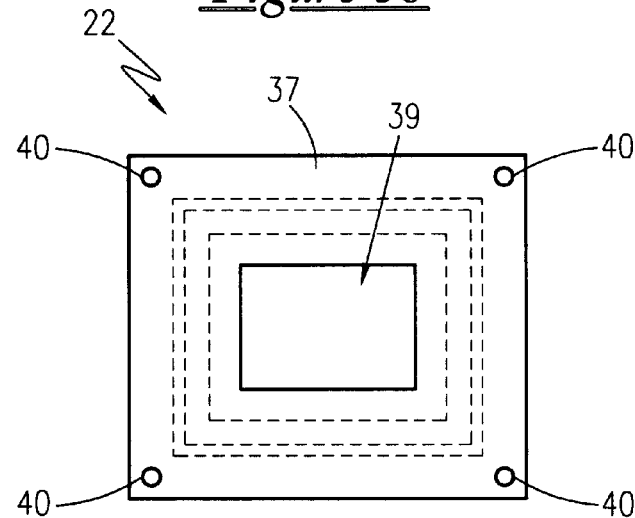
FIG. 3c is right end view of the mounting extension portion of the high temperature insertion type flow element and mounting extension with outboard end supports, according to the preferred embodiment of the present invention.
Figure 4:
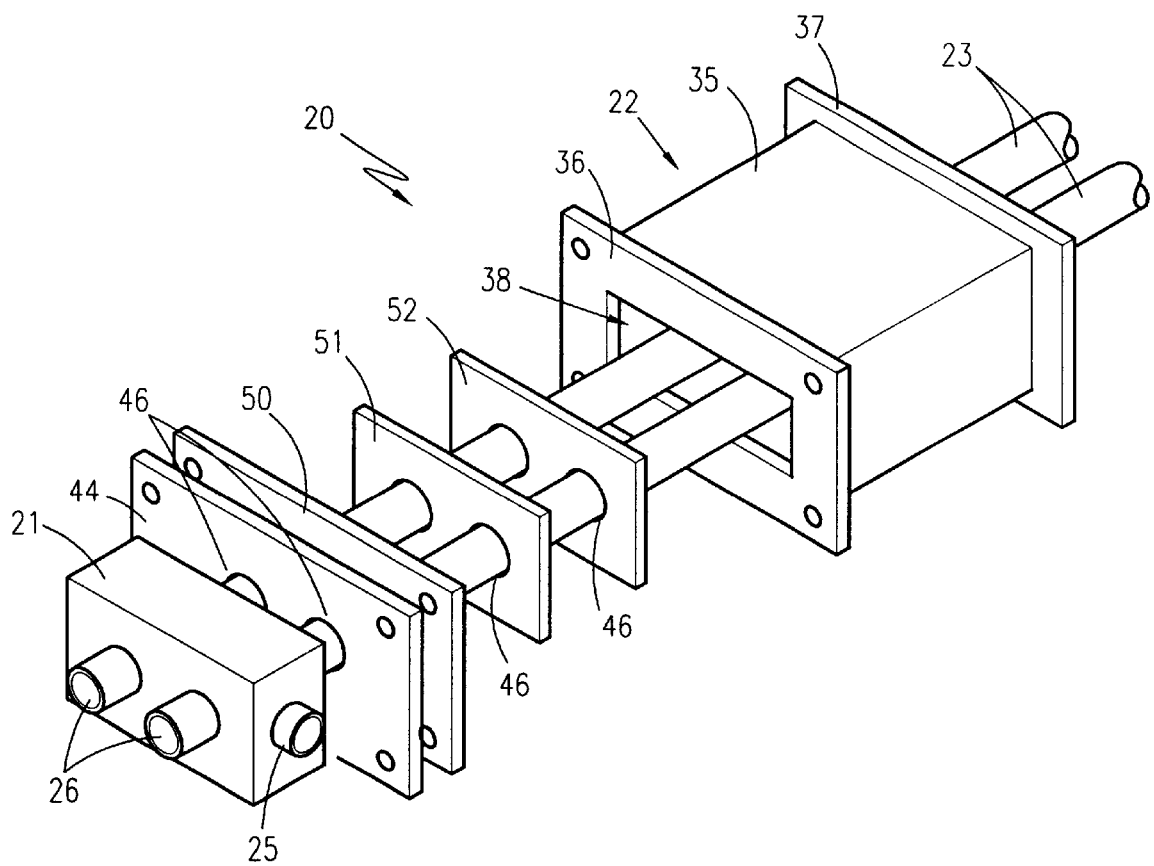
FIG. 4 is an exploded perspective view of the high temperature insertion type flow element and mounting extension, according to the preferred embodiment of the present invention.
Figure 5:
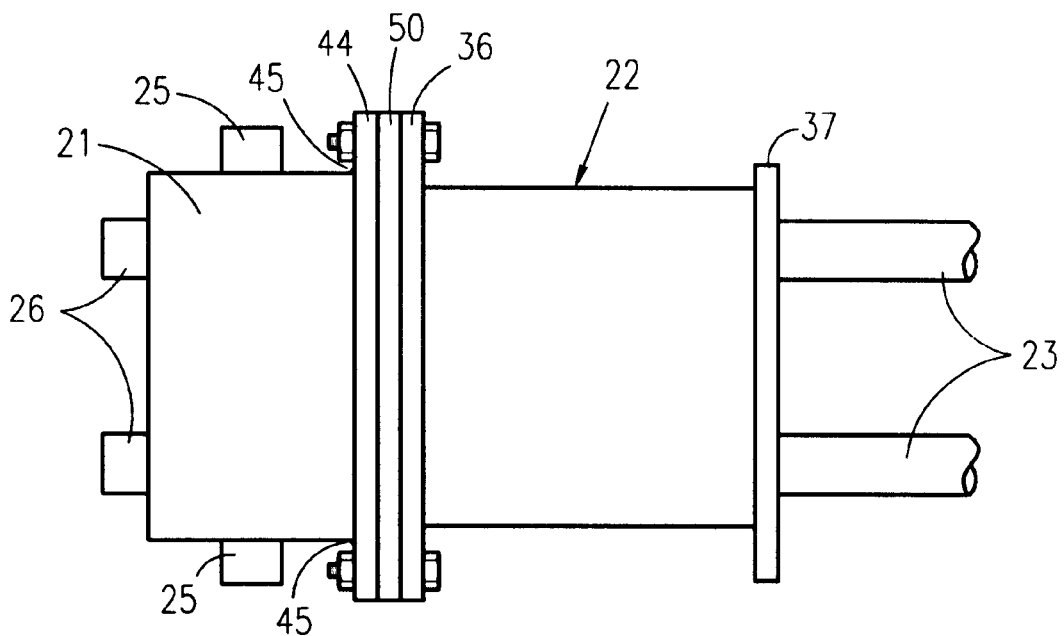
FIG. 5 is a horizontal view of the high temperature insertion type flow element and mounting extension depicting the installation of the element head/mounting extension combination, according to the preferred embodiment of the present invention.
Figure 6:
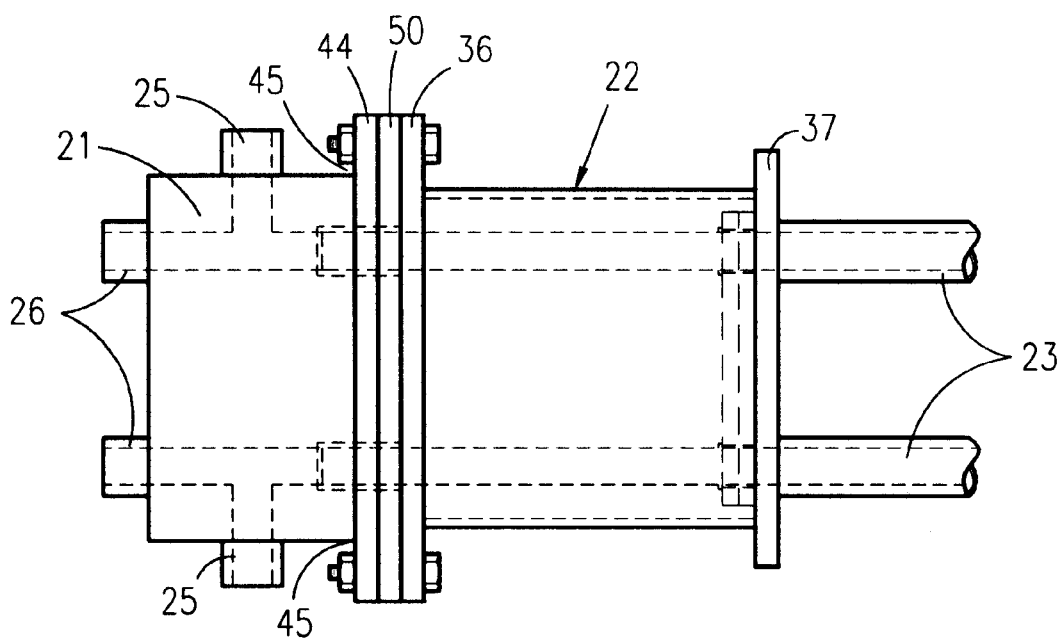
FIG. 6 is a horizontal plan view of the high temperature insertion type flow element and mounting extension depicting the installation of the element head/mounting extension combination, according to the preferred embodiment of the present invention.
Figure 7:
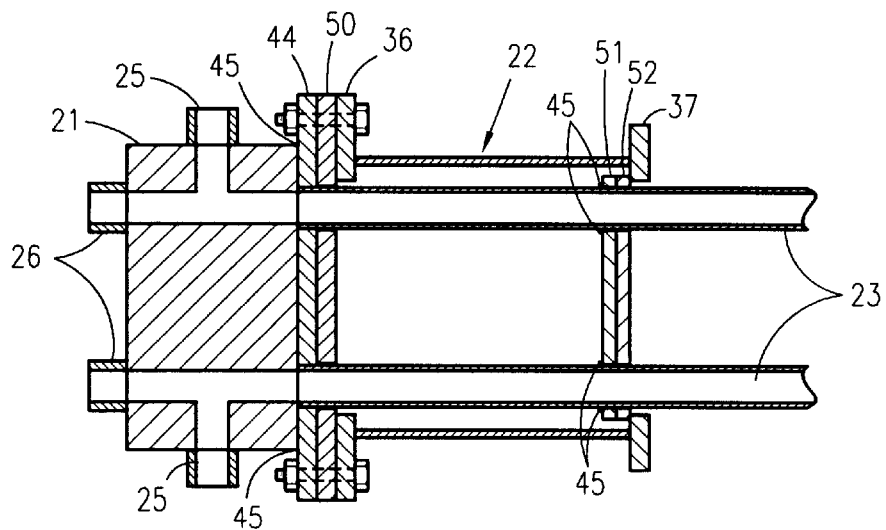
FIG. 7 is a horizontal sectional view of the high temperature insertion type flow element and mounting extension depicting the installation of the element head/mounting extension combination, according to the preferred embodiment of the present invention.

Referring now to FIGS. 3a, 3b, and 3c, depicted is the mounting extension 22 portion of the high temperature flow element 20, according to the preferred embodiment of the present invention. The mounting extension consists of a tubular housing 35 having a rectangular cross section. An element head support flange 36 and a mounting extension support flange 37 are mounted at opposite ends of the tubular housing 35, oriented perpendicular to its longitudinal axis.

The element head support flange 36 provides a flat, rectangular surface upon which to mount the element head 21 and includes a rectangular first element tube aperture 38 bored therethrough. Although various conventional fastening means could be used to accomplish the fastening of the element head 21 to the element head support flange 36, in the preferred embodiment, the element head 21 is welded to an element head mounting plate (not shown in these Figures) having a rectangular shape that mates with that of the element head support flange 36. The element head support flange 36 includes a series of fastener apertures 40 that allow for securing the element head 21 to the mounting extension 22 via the element head mounting plate 36, using conventional threaded fasteners (not shown in these Figures).

The mounting extension support flange 37 provides a means by which to secure the mounting extension 22 and, thus, the high temperature flow element 20 to the exterior surface of a duct wall. The mounting extension support flange includes a rectangular second element tube aperture 39 bored therethrough. For purposes explained in further detail herein below, the rectangular dimensions of the second element tube aperture 39 are smaller than the rectangular dimensions of the first element tube aperture 38. As is the case with the element head support flange 36, various conventional fastening means could be used to accomplish the fastening of the mounting extension 22 to the duct wall. In the preferred embodiment, the mounting extension support flange 37 is welded to the duct wall, so as to provide a secure fit with an air-tight seal. Nevertheless, the mounting extension support flange 37 is optionally fit with a series of fastener apertures 40 that allow for securing the mounting extension 22 via conventional threaded fasteners.

Referring now to FIGS. 4–7, depicted is the assembly of the element head 21, the mounting extension 22 and the element tubes 23 of the high temperature flow element 20, according to the preferred embodiment of the present invention. In the preferred embodiment, the element head is secured to the element head mounting plate 44 using a welded bead 45. The element tubes are passed through element tube apertures 46 and secured to the element head 21 via a welded bead or other suitable fastening means. An element head gasket 50 is then slid over the element tubes 23, followed by an extension housing sealing plate 51 and an extension housing sealing gasket 52. The element head gasket 50, extension housing sealing plate 51 and the extension housing sealing gasket 52 also incorporate element tube apertures 46 that allow the passage of the element tubes 23 therethrough.

The purpose of the extension housing sealing plate 51 and the extension housing sealing gasket is to form an airtight seal between the extension housing 22 and the interior cavity of the duct to which it is attached. The seal prevents turbulence that would occur as a result of gasses flowing past an open element housing, producing errors in the flow measurement capabilities of the high temperature flow element 20. The element head gasket 50 and the extension housing sealing gasket 52 are constructed of an insulating material that prevents thermal losses through the mounting extension. The rectangular dimensions of the extension housing sealing plate 51 and the extension housing sealing gasket 52 are such that they pass freely through the first element tube aperture 38, but not through the second element tube aperture 39. Thus, an interference fit is formed between the interior surface of the mounting extension support flange 37 and the extension housing sealing plate 51/extension housing sealing gasket 52. The extension housing sealing plate 51 is welded to the element tubes 23 at a position such that, when the element head mounting plate 44 is fastened to the element head support flange 36, the extension housing sealing gasket 52 is sandwiched between the extension housing sealing plate 51 and the interior surface of the mounting extension support flange 37, creating an insulated air-tight seal.

Figure 8:
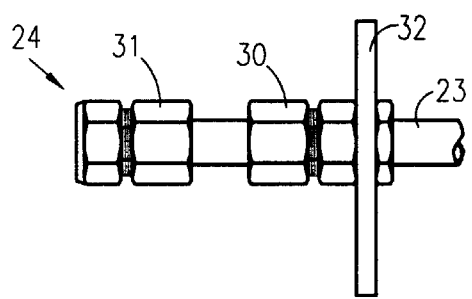
FIG. 8 is a horizontal plan view of the outboard access port and support for use with the high temperature insertion type flow element and mounting extension as depicted in FIG. 2a, according to the preferred embodiment of the present invention.

Referring now to FIG. 8, depicted is the outboard support 24 for use with the high temperature flow element 20 as depicted in FIG. 2a, according to the preferred embodiment of the present invention. The outboard support 24 consists of an outboard support fitting 30, an outboard access port 31, and an outboard support plate 32. The outboard support fitting 30 is a modified compression type fitting that replaces the compression ferrule typically found in such a fitting with a high-temperature packing (not shown in FIG. 8) that forms a tight seal while allowing the element tube 23 to slide therein, thus absorbing thermal expansion. The compression fitting incorporated into the design of the outboard support fitting 30 will be discussed in further detail herein below. The outboard support fitting 30 secures the element tubes 23 to the outboard support plate 32 that is secured to the exterior surface of the duct wall via conventional fastening means. The outboard access port 31 consists of a conventional compression fitting 60 that is secured to the element tube and a cap 61 that seals the outboard access port 31. In situations where a high concentration of particulate matter in the measured gasses tends to clog the element tubes 23, removal of the cap 61 allows for cleaning and maintenance of the element tubes 23.

Figure 9:
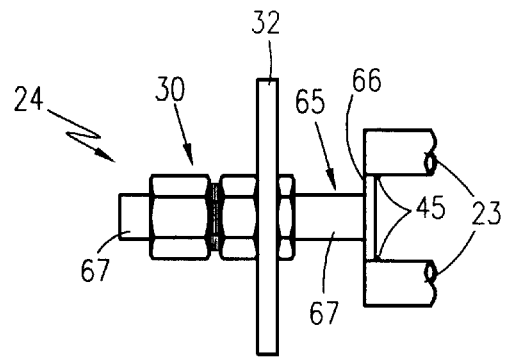
FIG. 9 is a horizontal plan view of the outboard end support for use with the high temperature insertion type flow element and mounting extension as depicted in FIG. 2b, according to the preferred embodiment of the present invention.

Referring now to FIG. 9, depicted is the outboard support 24 for use with the high temperature flow element 20 as depicted in FIG. 2b, according to the preferred embodiment of the present invention. The outboard support 24 consists of an outboard support fitting 30, an outboard support plate 32 and a element tube support bracket 65. The element tube support bracket 65 consists of a cross-member 66 that spans between the ends of the element tubes 23 and is connected thereto via a welded bead 45 or other conventional fastening means. The cross-member 66 is connected to an anchoring rod 67 that is connected to the outboard support fitting 30. The outboard support fitting 30 is a modified compression type fitting that replaces the compression ferrule typically found in such a fitting with a high-temperature packing (not shown in FIG. 9) that forms a tight seal while allowing the anchoring rod 67 to slide therein, thus absorbing the thermal expansion of the element tubes 23. The compression fitting incorporated into the design of the outboard support fitting 30 will be discussed in further detail herein below. The outboard support fitting 30 secures the element tube support bracket 65 and, thus, the element tubes 23 to the outboard support plate 32 that is secured to the exterior surface of the duct wall via conventional fastening means.

Figure 10:
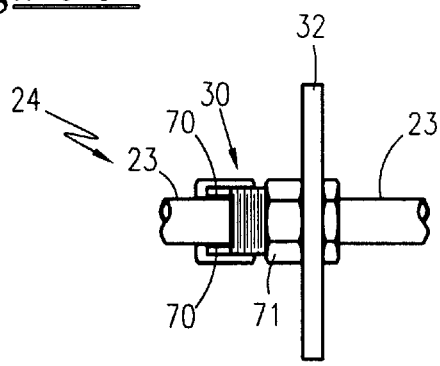
FIG. 10 is a horizontal sectional view of the outboard support for use with the high temperature insertion type flow element and mounting extension as depicted in FIGS. 8 and 9, according to the preferred embodiment of the present invention.

Referring now to FIG. 10, depicted is a sectional view of the outboard support 24 showing the internal construction of the outboard support fitting 30, according to the preferred embodiment of the present invention. As previously stated, the construction of the outboard support fitting 30 consists of a modified compression fitting that allows for the thermal expansion of the element tubes 23 or anchoring rod 67, depending upon the style of the outboard support 24. As is shown, a high-temperature packing 70 replaces the compression ferrule. While it is envisioned that a ribbon packing or packing ring made of any pliable material resistant to high temperatures can be used to construct the high-temperature packing 70, in the preferred embodiment, a GRAPHOIL (tm) packing material, as manufactured by U-CAR (tm), or similar and equivalent material has been found to be successful in permanently "sealing" the element tubes 23, thereby assuring a high pressure seal such that the outboard support fitting 30 retains its integrity and remains leak-free even under conditions of extreme temperature or extreme temperature gradient cycling. The element tube 23 is passed through a compression sleeve 71 and a compression cap 72 threadably fastened to the compression sleeve 71. The element tube 23 is encased with the high-temperature packing 70 between the compression sleeve 71 and the compression cap 72. As the compression cap 72 is tightened, the high-temperature packing 70 is compressed within the outboard support fitting 30, both sealing and securing the element tube 23 therein. The high-temperature packing 70 remains pliable, forming a seal around the element tubes 23, while still permitting the lateral motion encountered when thermal differential expansion occurs.

2. Operation of the Preferred Embodiment

Figure 11:
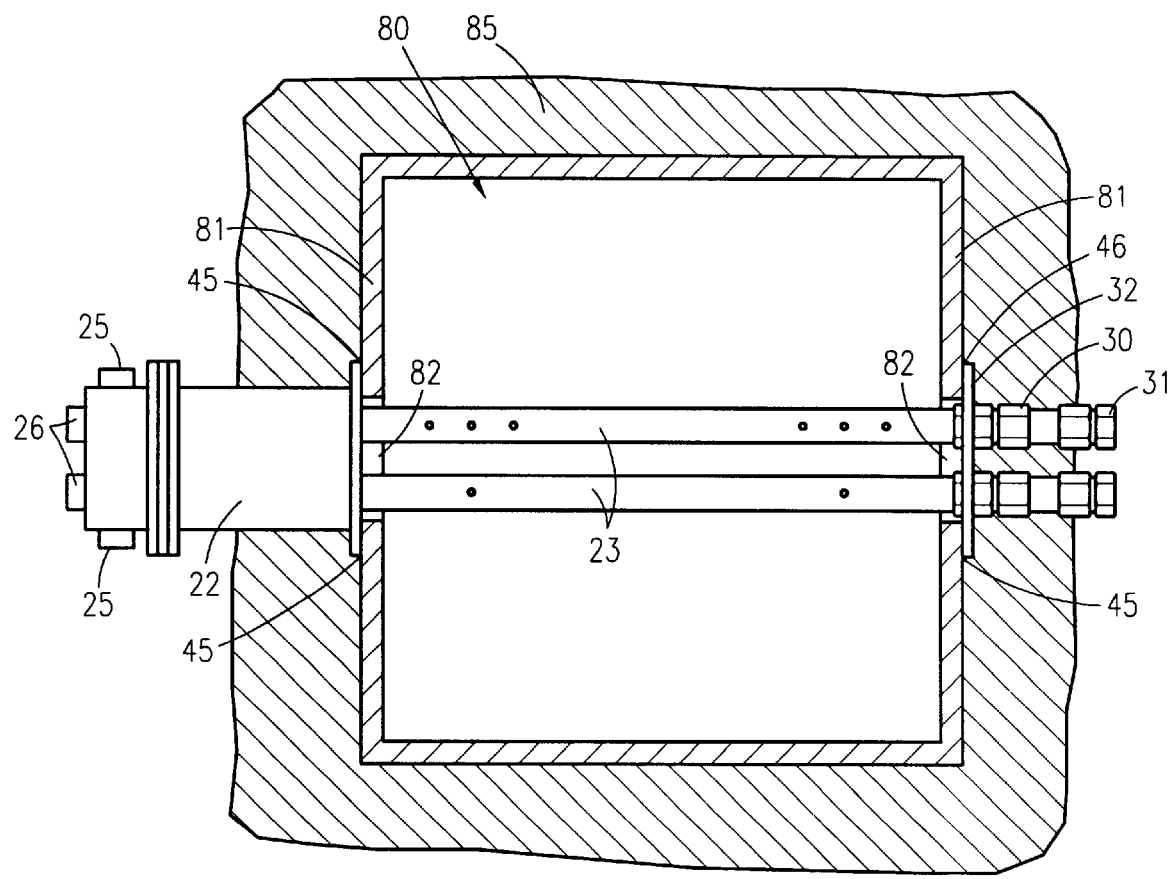
FIG. 11 is a horizontal plan view depicting the installation of the high temperature insertion type flow element and mounting extension with outboard access ports and supports as shown in FIG. 2a, according to the preferred embodiment of the present invention.
Figure 12:
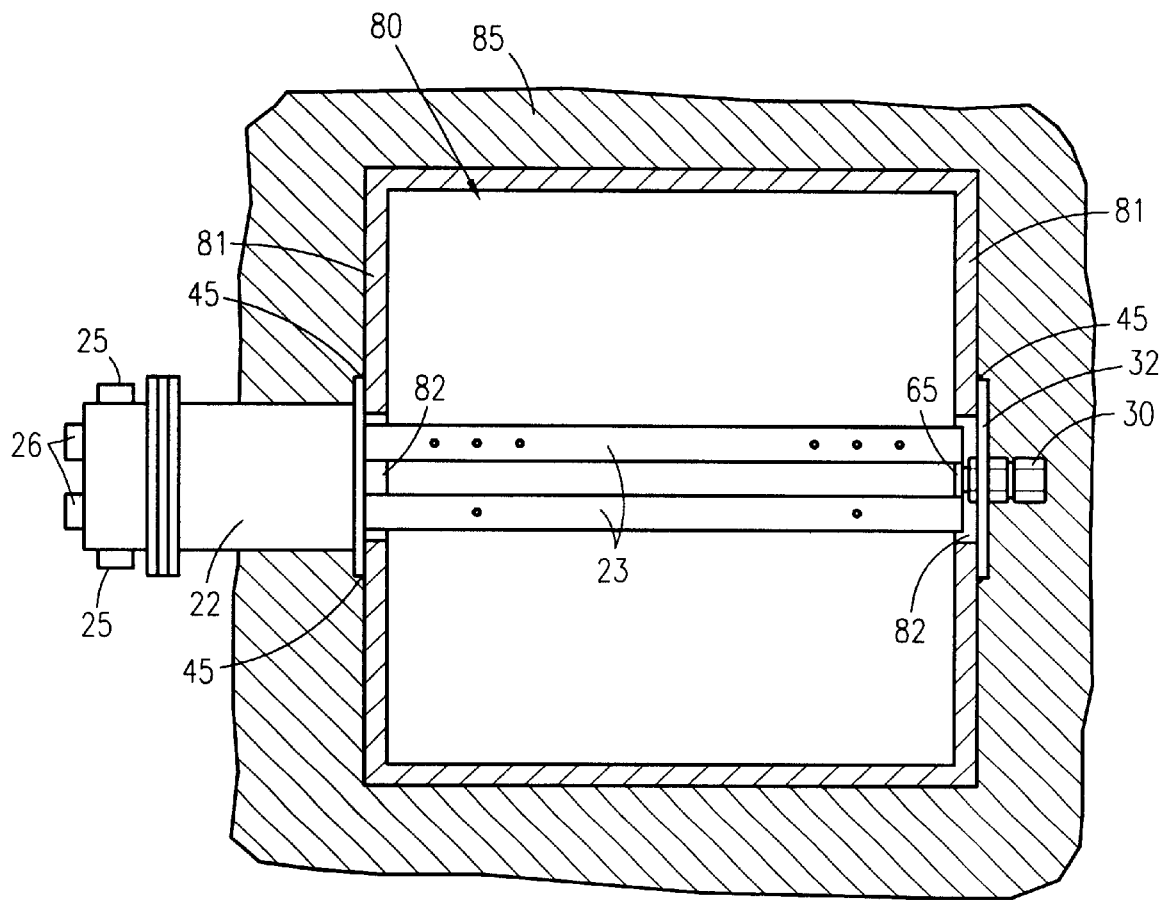
FIG. 12 is a horizontal plan view depicting the installation of the high temperature insertion type flow element and mounting extension with outboard support as shown in FIG. 2b, according to the preferred embodiment of the present invention.

In accordance with a preferred embodiment of the present invention, as shown in FIGS. 11 and 12, the high temperature flow element 20 is used in the following manner. The high temperature flow element 20 is installed in a duct 80, securing it to opposing duct walls 81. Insertion apertures 82 are cut in the duct walls 81, allowing the element tubes 23 to pass freely therethrough. Once in place within the duct 80, the high temperature flow element is secured therein by attaching the mounting extension support flange 37 and the outboard support plate 32 to the duct walls 81 via a welded bead 45 or other conventional fastening means, forming an airtight seal. As described herein above the outboard support fittings 30, extension housing sealing plate 51 and the extension housing sealing gasket 52 serve to complete the sealing of the high temperature flow element 20 within the duct 80. Installed in the aforementioned manner, the instrumentation ports 25 are connected to instrumentation equipment, thus providing a differential pressure reading that can be used to calculate a gas flow rate within the duct 80. When the element tubes 23 need cleaned, access is provided via the cleaning ports 26 or the outboard access ports 31, depending upon the specific configuration of the outboard support 24. The inclusion of the cleaning ports 26 as an integrated feature of the element head drastically cuts the costs associated with conventional cleaning methods. The mounting extension 22 places the element head 21, the instrumentation ports 25 and the cleaning ports 26 in a position outside of any insulating materials 85 encasing the duct 80, providing unobstructed access.

While the preferred embodiments of the invention have been shown, illustrated, and described, it will be apparent to those skilled in this field that various modifications may be made in these embodiments without departing from the spirit of the present invention. By way of example, while two variations of the outboard support 24 have been described herein above, it is envisioned that a variety of configurations incorporating the design of the outboard support fitting 30 would be equally effective. Furthermore, applications are envisioned wherein the advantages of the integrated cleaning port head would be of beneficial use while the mounting extension is not expressly required. It is for this reason that the scope of the invention is set forth in and is to be limited only by the following claims.

What is claimed is:

1. A high temperature flow element comprising:
   a mounting extension comprising a tubular housing having a head end opposite a mounting end forming a hollow interior cavity there between;
   an element head having a first instrument port in fluid communication with a first cleaning port and a first element connection port and a second instrument port in fluid communication with a second cleaning port and a second element connection port, said element head connected to said head end such that said first and second element connection ports are in fluid connectivity with said hollow interior cavity;
   a first flow element tube having a first proximal end opposite a first distal end, said first proximal end attached to said first element connection port, said first flow element passing through said hollow interior cavity and exiting through said mounting end;
   a second flow element tube having a second proximal end opposite a second distal end, said second proximal end attached to said second element connection port, said second flow element passing through said hollow interior cavity and exiting through said mounting end; and
   an outboard support comprising an outboard support plate supporting at least one outboard support fitting, said outboard support fitting further comprising a modified compression fitting that secures said first and second distal ends, forming a tight, reliable seal while permitting longitudinal thermal expansion of said first and second flow element tubes;
   a gas flow duct having a high temperature flow element affixed thereto, passing through a first insertion aperture in the duct sidewall, traversing the interior of said gas flow duct and exiting through a second insertion aperture in the opposing duct sidewall, said mounting end affixed to the exterior surface of said gas flow duct at said first insertion aperture and said outboard support plate affixed to the exterior surface of said gas flow duct at said second insertion aperture, said mounting extension positioning said element head in an offset manner so as to provide access free from obstruction by duct insulating materials, said outboard support fitting allowing for a longitudinal thermal expansion of said first and second element tubes.

2. The high temperature flow element of claim 1 wherein said first and second cleaning ports further comprise a removable sealing means that can be removed, providing access to said first and second flow element tubes for cleaning and maintenance purposes.

3. The high temperature flow element of claim 1 wherein said first and second element tubes are connected to pressure sensing devices by way of said first and second instrumentation ports and providing a differential pressure reading used to calculate a gas flow within said gas flow duct.

4. The high temperature flow element of claim 1 wherein said first and second element tubes further comprise Pitot tubes.

5. The high temperature flow element of claim 1 wherein said modified compression fitting further comprises a high-temperature tubing connection for affixing said first and second distal ends to said outboard support plate, said high temperature tubing connection comprising a compression fitting seated around a ribbon packing or packing ring made of any pliable material resistant to high temperatures.

6. The high temperature flow element as described in claim 5, wherein said ribbon packing or packing ring is comprised of GRAPHOIL (tm) packing material, as manufactured by U-CAR (tm), or similar and equivalent material.

7. An improved flow element wherein a flow element is modified so as to produce a high temperature flow element for use in high temperature processes, said high temperature flow element comprising:
   a mounting extension comprising a tubular housing having a head end opposite a mounting end forming a hollow interior cavity there between; and
   an outboard support comprising an outboard support plate supporting at least one outboard support fitting, said outboard support fitting further comprising a modified compression fitting;
   wherein a flow element is used in conjunction with said mounting extension and said outboard support, said flow element comprising:
      an element head having a first instrument port in fluid communication with a first cleaning port and a first element connection port and a second instrument port in fluid communication with a second cleaning port and a second element connection port;
      a first flow element tube having a first proximal end opposite a first distal end, said first proximal end attached to said first element connection port, said first flow element passing through said hollow interior cavity and exiting through said mounting end; and
      a second flow element tube having a second proximal end opposite a second distal end, said second proximal end attached to said second element connection port, said second flow element passing through said hollow interior cavity and exiting through said mounting end;
      wherein said element head is connected to said head end such that said first and second element connection ports are in fluid connectivity with said hollow interior cavity and said outboard support supports said first and second flow element tubes, said modified compression fitting forming a tight, reliable seal while permitting longitudinal thermal expansion of said first and second flow element tubes; and a gas flow duct having a high temperature flow element affixed thereto, passing through a first insertion aperture in the duct sidewall, traversing the interior of said gas flow duct and exiting through a second insertion aperture in the opposing duct sidewall, said mounting end affixed to the exterior surface of said gas flow duct at said first insertion aperture and said outboard support plate affixed to the exterior surface of said gas flow duct at said second insertion aperture, said mounting extension positioning said element head in an offset manner so as to provide access free from obstruction by duct insulating materials, said outboard support fitting allowing for the longitudinal thermal expansion of said first and second element tubes.

8. The high temperature flow element of claim 7 wherein said first and second cleaning ports further comprise a removable sealing means that can be removed, providing access to said first and second flow element tubes for cleaning and maintenance purposes.

9. The high temperature flow element of claim 7 wherein said first and second element tubes are connected to pressure sensing devices by way of said first and second instrumentation ports and providing a differential pressure reading used to calculate the gas flow within said gas flow duct.

10. The high temperature flow element of claim 7 wherein said first and second element tubes further comprise Pitot tubes.

11. The high temperature flow element of claim 7 wherein said modified compression fitting further comprises a high-temperature tubing connection for affixing said first and second distal ends to said outboard support plate, said high temperature tubing connection comprising a compression fitting seated around a ribbon packing or packing ring made of any pliable material resistant to high temperatures.

12. The high temperature flow element as described in claim 11, wherein said ribbon packing or packing ring is comprised of GRAPHOIL (tm) packing material, as manufactured by U-CAR (tm), or similar and equivalent material.

13. A high temperature flow element comprising:
an element head having a first instrument port in fluid communication with a first cleaning port and a first element connection port and a second instrument port in fluid communication with a second cleaning port and a second element connection port;
a first flow element tube having a first proximal end opposite a first distal end, said first proximal end attached to said first element connection port;
a second flow element tube having a second proximal end opposite a second distal end, said second proximal end attached to said second element connection port; and
an outboard support comprising an outboard support plate supporting at least one outboard support fitting, said outboard support fitting further comprising a modified compression fitting that secures said first and second distal ends, forming a tight, reliable seal while permitting longitudinal thermal expansion of said first and second flow element tubes;
a gas flow duct having a high temperature flow element affixed thereto, passing through a first insertion aperture in the duct sidewall, traversing the interior of said gas flow duct and exiting through a second insertion aperture in the opposing duct sidewall, said element head affixed to the exterior surface of said gas flow duct at said first insertion aperture and said outboard support plate affixed to the exterior surface of said gas flow duct at said second insertion aperture, said outboard support fitting allowing for the longitudinal thermal expansion of said first and second element tubes.

14. The high temperature flow element of claim 13 wherein said first and second cleaning ports further comprise a removable sealing means that can be removed, providing access to said first and second flow element tubes for cleaning and maintenance purposes.

15. The high temperature flow element of claim 13 wherein said first and second element tubes are connected to pressure sensing devices by way of said first and second instrumentation ports and providing a differential pressure reading used to calculate the gas flow within said gas flow duct.

16. The high temperature flow element of claim 13 wherein said first and second element tubes further comprise Pitot tubes.

17. The high temperature flow element of claim 13 wherein said modified compression fitting further comprises a high-temperature tubing connection for affixing said first and second distal ends to said outboard support plate, said high temperature tubing connection comprising a compression fitting seated around a ribbon packing or packing ring made of any pliable material resistant to high temperatures.

18. The high temperature flow element as described in claim 17, wherein said ribbon packing or packing ring is comprised of GRAPHOIL (tm) packing material, as manufactured by U-CAR (tm), or similar and equivalent material.

* * * * *